(12) United States Patent
Saga et al.

(10) Patent No.: US 11,033,661 B2
(45) Date of Patent: Jun. 15, 2021

(54) ANTI-ADHESION MATERIAL AND SUBSTITUTE BIOMEMBRANE USING DECELLULARIZED TISSUE

(71) Applicants: KM BIOLOGICS CO., LTD., Kumamoto (JP); ADEKA CORPORATION, Tokyo (JP); NATIONAL UNIVERSITY CORPORATION TOKYO MEDICAL AND DENTAL UNIVERSITY, Tokyo (JP); SAPPORO MEDICAL UNIVERSITY, Sapporo (JP)

(72) Inventors: Hideki Saga, Koshi (JP); Takanori Uchida, Kumamoto (JP); Shoko Tokorozaki, Shikokuchuo (JP); Ken-ichiro Hiwatari, Tokyo (JP); Haruki Obara, Kamisu (JP); Akio Kishida, Tokyo (JP); Tsuyoshi Kimura, Tokyo (JP); Jun Negishi, Ueda (JP); Tetsuya Higami, Sapporo (JP); Seiichi Funamoto, Tokyo (JP)

(73) Assignees: ADEKA CORPORATION, Tokyo (JP); NATIONAL UNIVERSITY CORPORATION TOKYO MEDICAL AND DENTAL UNIVERSITY, Tokyo (JP); SAPPORO MEDICAL UNIVERSITY, Hokkaido (JP)

(*) Notice: Subject to any disclaimer, the term of this patent is extended or adjusted under 35 U.S.C. 154(b) by 173 days.

(21) Appl. No.: 15/556,776

(22) PCT Filed: Mar. 7, 2016

(86) PCT No.: PCT/JP2016/057014
§ 371 (c)(1),
(2) Date: Sep. 8, 2017

(87) PCT Pub. No.: WO2016/143746
PCT Pub. Date: Sep. 15, 2016

(65) Prior Publication Data
US 2018/0078679 A1    Mar. 22, 2018

(30) Foreign Application Priority Data
Mar. 12, 2015 (JP) .............................. JP2015-049922

(51) Int. Cl.
A61L 31/04 (2006.01)
A61L 31/10 (2006.01)
A61L 31/00 (2006.01)
A61L 24/10 (2006.01)

(52) U.S. Cl.
CPC .......... *A61L 31/046* (2013.01); *A61L 31/005* (2013.01); *A61L 31/10* (2013.01); *A61L 24/106* (2013.01); *A61L 2300/424* (2013.01)

(58) Field of Classification Search
CPC ............ A61L 2300/424; A61L 24/106; A61L 31/005; A61L 31/046; A61L 31/10
See application file for complete search history.

(56) References Cited

U.S. PATENT DOCUMENTS

| | | | |
|---|---|---|---|
| 4,801,299 A | 1/1989 | Brendel et al. | |
| 6,074,663 A | 6/2000 | Delmotte et al. | |
| 6,187,039 B1 | 2/2001 | Hiles et al. | |
| 6,254,627 B1 | 7/2001 | Freidberg | |
| 6,376,244 B1 | 4/2002 | Atala | |
| 6,509,145 B1 | 1/2003 | Torrianni | |
| 6,613,325 B1 | 9/2003 | Amery et al. | |
| 8,486,139 B2 | 7/2013 | Kishida et al. | |
| 8,883,210 B1 | 11/2014 | Truncale et al. | |
| 9,023,273 B2 | 5/2015 | Kibalo | |
| 2001/0044654 A1* | 11/2001 | Chen .................. | A61L 27/3625 623/1.41 |
| 2002/0001584 A1 | 1/2002 | Metzner et al. | |
| 2006/0110720 A1 | 5/2006 | Fujisato et al. | |
| 2007/0269791 A1 | 11/2007 | Takami et al. | |
| 2010/0179639 A1 | 7/2010 | Bloor et al. | |

(Continued)

FOREIGN PATENT DOCUMENTS

| | | |
|---|---|---|
| CA | 2 894 145 | 7/2014 |
| CN | 1618954 | 5/2005 |

(Continued)

OTHER PUBLICATIONS

International Search Report dated Apr. 26, 2016 in International (PCT) Application No. PCT/JP2016/057014.

(Continued)

*Primary Examiner* — Blaine Lankford (57) ABSTRACT

An anti-adhesion material comprising decellularized tissues and a biocompatible polymer or fibrin glue; a method for preparing an anti-adhesion material comprising complexing a biocompatible polymer or fibrin glue to decellularized tissues; an anti-adhesion material kit comprising decellularized tissues and a biocompatible polymer or fibrin glue; a substitute biomembrane comprising decellularized tissues and a biocompatible polymer or fibrin glue; a method for preparing a substitute biomembrane comprising complexing a biocompatible polymer or fibrin glue to decellularized tissues; and a substitute biomembrane kit comprising decellularized tissues and a biocompatible polymer or fibrin glue.

28 Claims, 1 Drawing Sheet

(56) References Cited

U.S. PATENT DOCUMENTS

| | | | |
|---|---|---|---|
| 2010/0190254 A1* | 7/2010 | Chian | A61L 27/3847 |
| | | | 435/396 |
| 2011/0054588 A1 | 3/2011 | Xu et al. | |
| 2012/0064050 A1* | 3/2012 | Calle | A61K 35/42 |
| | | | 424/93.21 |

FOREIGN PATENT DOCUMENTS

| | | |
|---|---|---|
| CN | 103405811 | 11/2013 |
| JP | 59-160465 | 9/1984 |
| JP | 60-501540 | 9/1985 |
| JP | 11-502431 | 3/1999 |
| JP | 2000-116765 | 4/2000 |
| JP | 2001-327592 | 11/2001 |
| JP | 2002-507907 | 3/2002 |
| JP | 2003-500170 | 1/2003 |
| JP | 2003-518981 | 6/2003 |
| JP | 2003-525062 | 8/2003 |
| JP | 2004-51531 | 2/2004 |
| JP | 2004-65780 | 3/2004 |
| JP | 2004-97552 | 4/2004 |
| JP | 2005-185507 | 7/2005 |
| JP | 2005-211480 | 8/2005 |
| JP | 2007-268239 | 10/2007 |
| JP | 2009-50297 | 3/2009 |
| JP | 2010-221012 | 10/2010 |
| JP | 2010-284216 | 12/2010 |
| JP | 2013-502275 | 1/2013 |
| JP | 2013-503696 | 2/2013 |
| JP | 2013-226166 | 11/2013 |
| WO | 84/04880 | 12/1984 |
| WO | 99/00152 | 1/1999 |
| WO | 03/084410 | 10/2003 |
| WO | 2008/111530 | 9/2008 |
| WO | 2009/025398 | 2/2009 |
| WO | 2014/034759 | 3/2014 |

OTHER PUBLICATIONS

International Preliminary Report on Patentability dated Sep. 14, 2017 in International (PCT) Application No. PCT/JP2016/057014.
Fukushima et al., "Prevention of adhesive ileus with adhesion preventive materials", Surgical Therapy, 94(6):919-924 (2006), with English Abstract.
Fujishita et al., "A study of prevention of adhesion after uterine myoma enucleation", Gynecologic and Obstetric Surgery, 13:91-98 (2002), with English Abstract.
Dobell et al., "Catastrophic Hemorrhage during Redo Sternotomy", The Annals of Thoracic Surgery, 37(4):273-278 (1984).
Cunningham et al., "Influence of primary closure of the pericardium after open-heart surgery on the frequency of tamponade, postcardiotomy syndrome, and pulmonary complications", The Journal of Thoracic and Cardiovascular Surgery, 70:119-125 (1975).
Sakuma et al., "Closure of the Pericardium Using Synthetic Bioabsorbable Polymers", Japan Journal of Artificial Organs, 29(1):223-238 (2000), with English Abstract.
Ray et al., "Abdominal Adhesiolysis: Inpatient Care and Expenditures in the United States in 1994", J. Am. Coll. Surg., 186:1-9 (1998).
Lodge et al., "A Novel Bioresorbable Film Reduces Postoperative Adhesions After Infant Cardiac Surgery", Ann Thorac Surg., 86:614-621 (2008).
Haensing et al., "Bioresorbable adhesion barrier for reducing the severity of postoperative cardiac adhesions: Focus on REPEL-CV", Medical Devices: Evidence and Research, 4:17-25 (2011).
Sato et al., "Etiology and prevention of postoperative adhesion", Obstet. Gynecol. (Tokyo), 57(12):2398-2404 (1990), with English Abstract.
Okuda et al., "A new technique for reproductive organ-preserving surgery", World of Obstetrics and Gynecology, 45(9):759-764 (1993), with English Abstract.
Tomizawa et al., "Antiadhesive Pericardium with Heparin Slow Release", Japanese Abstract Journal of Artificial Organs, 17(2):566-569 (1988), with English Abstract.
Noishiki et al., "Heparin Slow Release Antiadhesive Pericardium with Natural Tissue Elasticity", Japanese Journal of Artificial Organs, 17(2):578-581 (1988), with English Abstract.
Miyata et al., "A Biodegradable Antiadhesion Collagen Membrane with Slow Release Heparin", ASAIO Transactions 34(3):687-691 (1988).
Miyata et al., "Biodegradable Antiadhesive Membrane", Japanese Journal of Artificial Organs, 18(1):93-96 (1989), with English Abstract.
Furuse et al., "Antiadhesive Collagen Membrane with Heparin Slow Release Using New Heparinization Method by Anchoring Reagent Glycidyl Trimethyl Ammonium Chloride", Japanese Journal of Artificial Organs, 16(3):1350-1353 (1987), with English Abstract.
Noishiki et al., "Heparin releasing antiadhesive membrane", Japanese Journal of Artificial Organs, 14(2):788-791 (1985), with English Abstract.
Matsushima et al., "Decellularized dermis-polymer complex provides a platform for soft-to-hard tissue interfaces", Materials Science and Engineering C, 35:354-362 (2014).
Nam et al., "In Vivo Characterization of a Decellularized Dermis-Polymer Complex for Use in Percutaneous Devices", Artificial Organs, 38(12):1060-1065 (2014).
Matsushima et al., "Preparation of percutaneous device by incorporating polymer with decellularized tissue composite", Dai 27 Kai the Society of Life Support Technology Taikai (ABML2011), OS2-4, pp. OS2-4-1 to OS2-4-2 (2011), with English Abstract.
Kimura et al., "New attempt for preventing postoperative intraperitoneal adhesion using fibrin film", Acta Obstetrica et Gynaecologia Japonica, 41:No. Supplement, p. S-325, 450, (1989), with English Abstract.
Hashimoto et al., "A Case of Superficial Esophageal Carcinoma with Mucinous Cystis Tumor of the Pancreas", The Journal of the Japanese Practical Surgeon Society, 57(12):3000-3004 (1996), with English Abstract.
Okazaki et al., "Study of the effect of peritoneal adhesion prevention after surgery by spraying tissue adhesive", Japan Society of Gynecologic and Obstetric Endoscopy and Minimally Invasive Therapy, 8)1):111 (1992), with English Abstract.
Extended European Search Report dated Aug. 5, 2016 in European Application No. 13871129.6.
International Search Report dated Apr. 1, 2014 in International (PCT) Application No. PCT/JP2013/083749.
L'Heureux et al., "Tissue-Engineered Blood Vessel for Adult Arterial Revascularization", The New England Journal of Medicine, 357(14):1451-1453 (2007).
McAllister et al., "Effectiveness of Haemodialysis Access with an Autologous Tissue-Engineered Vascular Graft: A Multicentre Cohort Study", The Lancet, 373(Issue 9673):1440-1446 (2009).
Gauvin et al., "A Novel Single-Step Self-Assembly Approach for the Fabrication of Tissue-Engineered Vascular Constructs", Tissue Engineering: Part A, 16(5):1737-1747 (2010).
Office Action dated Aug. 8, 2016 in Australian Application No. 2013373262.
First Office Action dated Mar. 24, 2016 in Chinese Application No. 201380069242.X, with English Translation.
Office Action dated Sep. 15, 2016 in U.S. Appl. No. 14/650,051.
Notice of Allowance dated Jan. 11, 2017 in U.S. Appl. No. 14/650,051.
International Preliminary Report on Patentability dated Jul. 14, 2015 in International (PCT) Application No. PCT/JP2013/083749.
Extended European Search Report dated Oct. 30, 2018 in corresponding European patent application No. 16761714.1.
Office Action dated Dec. 25, 2019 in corresponding Chinese Patent Application No. 201680014927.8, with English translation.
Office Action dated Feb. 23, 2021 in corresponding Chinese Patent Application No. 201680014927.8, with English Translation, 24 pages.
Wang et al., "Practical Obstetrics and Gynecology Interventional Surgery 1st Edition", People's Military Medical Publishing House, Jun. 30, 2011, pp. 233-234.
Tian et al., "738 Questions from an Orthopedic Physician 1st Edition", Military Medical Science Press, Oct. 31, 2012, p. 101.

(56) References Cited

OTHER PUBLICATIONS

Wang et al., "Series of Difficult Surgical Skills in Spine Surgery, Surgical Techniques for Treatment of Spinal Tuberculosis 1st Edition", People's Military Medical Publishing House, Jul. 31, 2014, p. 361.

Lin et al., "Research Progress of Absorbable Film in Anti-Adhesion after Plastic Surgery", Jilin Medical Journal, vol. 30, No. 3, Feb. 28, 2009, pp. 281-283.

Xie et al., "Progress in Study on the Medical Materials of Anti-adhesive Absorbable Products and the Performance Requirements", China Medical Device Information, Aug. 31, 2012, pp. 10-18.

Zhao et al., "Advances in Resorbable Polymeric Materials for Prevention of Postoperation Adhesion", BME & Clin Med, vol. 7, No. 4, Dec. 31, 2003, pp. 236-240.

Office Action dated Sep. 18, 2020 in corresponding Chinese Patent Application No. 201680014927.8, with English Translation.

Ning et al., "Preparation and Biomechanic Assessment of Fibrin-binding Amniotic Membrane", Chinese Journal of Biomedical Engineering, 2008, vol. 27, No. 1, pp. 112-116.

Office Action dated Mar. 9, 2021 in corresponding Indian Patent Application No. 201747035418, 6 pages.

Noishiki et al., "Antiadhesive Collagen Membrane with Heparin Slow Release", Journal of Bioactive and Compatible Polymers, 1987, vol. 2, pp. 325-333.

\* cited by examiner

US 11,033,661 B2

ANTI-ADHESION MATERIAL AND SUBSTITUTE BIOMEMBRANE USING DECELLULARIZED TISSUE

TECHNICAL FIELD

The present invention relates to an anti-adhesion material, in particular, to a substitute biomembrane accompanied by tissue regeneration.

BACKGROUND ART

Postoperative tissue adhesion occurs in a broad area such as cardiovascular department, digestive surgery, orthopedics, obstetrics, ophthalmology, and the like. For instance, intraperitoneal adhesion after abdominal surgery is physiological reparation of the living body and it is difficult to completely prevent adhesion. Therefore, adhesive intestinal obstruction occurs at a fixed frequency due to postoperative adhesion. Adhesive intestinal obstruction is generally seen more in surgery to the lower abdomen where there are a lot of surfaces of dissection than in surgery to the upper abdomen. It is also said that its frequency is proportional to surgical time and an amount bleeding to some extent. For preventing or decreasing occurrence of adhesive intestinal obstruction, there are required careful and affectionate operation of surgeon, minimum surface of dissection, minimum bleeding, minimum operation time, prevention of contamination during operation, minimum remaining of a foreign matter, use of absorbable suture, appropriate drainage, prevention of infection, early postoperative ambulation, and the like. In the case of emergency contaminated operation, there are further required sufficient intraperitoneal washing, postoperative body position, postoperative use of antibiotics, and the like. Although each of these is effective for preventing adhesive intestinal obstruction to some extent, these are not sufficient for completely preventing occurrence of adhesive intestinal obstruction (Non-patent reference 1).

In the field of obstetrics, adhesion of the fallopian tube is one of the most important problems as it may lead to decrease in fecundity in future. To date, a variety of prevention of postoperative adhesion has been attempted but it is not that a perfect method for preventing adhesion has been established (Non-patent reference 2).

In the field of cardiovascular surgery, postoperative adhesion between the epicardium (the surface of the heart) and the chest walls and between the pericardium and the epicardium increases risk of damage to the heart and the large arteries during reoperation (Non-patent reference 3). Adhesion has an adverse effect on almost all the handlings during reoperation. Adhesion elicits bleeding due to adhesiotomy, damage to the organs and the vessels, and decreases visibility of a surface structure of the heart. Prolonged operation increases invasion to patients and increase in an amount of bleeding aggravates organ disorders associated with massive blood transfusion. When the epicardium and the chest walls are solidly adhered to each other after operation, contraction disorder of the heart, especially of the right ventricular, sometimes occurs. In this regard, it is preferable to form the conditions where the epicardium does not adhere to the surrounding structure and can move freely. It is thought that the self-pericardium, once opened, is preferably reclosed but there are many cases where it is not possible and in general it is not desirable to force reclosure (Non-patent reference 4). Therefore, after cardiotomy, some pericardium substitute material is often used for closure of the pericardium. For instance, silicon membrane, polyurethane, fascia, expanded-polytetrafluoroethylene (e-PTFE) sheet, heterogeneous pericardium from e.g. cow, pig, horse etc., Dacron, dura mater, and the like have been used. However, adhesion of the pericardium is severe and the use of foreign material may induce inflammation in the surrounding tissues and onset of mediastinitis (Non-patent reference 5). When remaining as a foreign matter, it becomes a hotbed of infectious bacteria and sometimes is calcified in a distant time. Therefore, development of a pericardium substitute material with high biocompatibility or a substitute biomembrane which accelerates regeneration is desired.

It is reported that 1.3 billion dollars were spent per year for the treatment of abdominal adhesion in the United States (Non-patent reference 6). Thus, from medical economic aspects, it is important to take a measure for alleviating adhesion as much as possible. Furthermore, by alleviating adhesion, improvement of QOL (Quality Of Life) of patients and reduction of medical expenses are expected. However, in the present circumstances, postoperative tissue adhesion cannot completely be prevented and is a big problem that bothers surgeons.

A physical barrier for preventing adhesion includes at present a barrier such as sodium hyaluronate/carboxymethyl cellulose (seprafilm (registered trade mark)) as a material, clinical use of which is domestically approved, and an anti-adhesion material such as oxidized regenerated cellulose (Interceed (registered trade mark)) and polytetrafluoroethylene (e-PTFE) (Gore-Tex Surgical Membrane (registered trade mark)). A substitute pericardium material approved in the United States includes an anti-adhesion material such as polylactic acid/polyethylene glycol (RE-PEL-CV (registered trade mark)). Effectiveness of any of these materials is limited and is not satisfactory for surgeons (Non-patent references 7-8). Gore-Tex Surgical Membrane (registered trade mark) remains permanently as a foreign matter and thus induces inflammation in the surrounding tissues and hyperplasia of fibrous tissues to make tissue composition not visible during reoperation. From these reasons as well, productization of a pericardium substitute material with high biocompatibility or a substitute biomembrane which accelerates regeneration is desired.

The use of fibrin glue, which is a tissue adhesive, for preventing adhesion is reported (Non-patent references 9-10). However, fibrin glue cannot completely prevent tissue adhesion and thus a big problem that bothers surgeons has not yet been solved.

Non-bioabsorbable material such as silicon, Teflon (registered trade mark) and polyurethane is highly effective for preventing adhesion between tissues but remains on the living tissue surface as being non-bioabsorbable not only to retard tissue repair but also to be a cause of inflammation. Therefore, an anti-adhesion membrane using bioabsorbable material, such as for instance, an anti-adhesion membrane using gelatin (Patent references 4-5), an anti-adhesion membrane using alginic acid or hyaluronic acid (Patent reference 6), an anti-adhesion membrane using carboxymethyl cellulose (Patent references 7-8) and the like have been developed. However, although the conventional bioabsorbable anti-adhesion membranes do not remain in the living body, they were problematic in that their anti-adhesion effect was insufficient and thus adhesion is likely to occur and that their strength is insufficient and thus suture to patients' tissues is not possible.

On the other hand, for preventing rejection in the case of transplantation of tissues from other people or animals of another species, decellularized tissues prepared by removing cells from biological tissues have been developed. A known method for decellularization includes a method using a surfactant (Patent references 9-10), a method using an enzyme (Patent reference 11), a method using an oxidizing agent (Patent reference 12), a method using treatment with a high hydrostatic pressure (Patent references 13-15), a method using freeze and thawing (Patent references 16-17), a method using treatment with hypertonic electrolyte solution (Patent reference 18), and the like. Application of decellularized tissues to the skin (Patent references 16-17), the cornea (Patent reference 14), the blood vessel (Patent reference 19) and the like is proposed.

Patent reference 1: Japanese Patent Publication No. 11-502431
Patent reference 2: Japanese Patent Publication No. 2001-327592
Patent reference 3: Japanese Patent Publication No. 2003-500170
Patent reference 4: Japanese Patent Publication No. 2004-065780
Patent reference 5: Japanese Patent Publication No. 2013-226166
Patent reference 6: Japanese Patent Publication No. 2000-116765
Patent reference 7: Japanese Patent Publication No. 2004-051581
Patent reference 8: Japanese Patent Publication No. 2010-284216
Patent reference 9: Japanese Patent Publication No. 60-501540
Patent reference 10: Japanese Patent Publication No. 2003-518981
Patent reference 11: Japanese Patent Publication No. 2002-507907
Patent reference 12: Japanese Patent Publication No. 2003-525062
Patent reference 13: Japanese Patent Publication No. 2004-097552
Patent reference 14: WO 2008/111530
Patent reference 15: Japanese Patent Publication No. 2013-502275
Patent reference 16: Japanese Patent Publication No. 2005-185507
Patent reference 17: Japanese Patent Publication No. 2005-211480
Patent reference 18: Japanese Patent Publication No. 2010-221012
Patent reference 19: Japanese Patent Publication No. 2013-503696
Non-patent reference 1: Tsuneo Fukushima et al., Surgical Therapy, 2006; 94(6):919-924
Non-patent reference 2: Akira Fujishita et al., Gynecologic and Obstetric Surgery, 2002; 13:91-98
Non-patent reference 3: Dobell A R., et al., Ann Thorac Surg. 1984; 37:273-8
Non-patent reference 4: Cunningham J N, Jr., et al., J Thorac Cardiovasc Surg. 1975; 70:119-25
Non-patent reference 5: Hiroshi Sakuma et al., Artificial Organs, 2000; 29(1):233-238
Non-patent reference 6: Ray NF. et al., J. Am. Coll. Surg. 1998; 186:1-9
Non-patent reference 7: Lodge A J, et al., Ann Thorac Surg. 2008; 86:614-621
Non-patent reference 8: Haensig et al., Medical Devices: Evidence and Research 2011; 4:17-25
Non-patent reference 9: Takamichi Sato et al., Obstetrics and Gynecology, 1990; 57(12):2398-2404
Non-patent reference 10: Kiyoji Okuda et al., The World of obstetrics and gynecology, 1993; 45(9):759-764

DISCLOSURE OF THE INVENTION

Technical Problem to be Solved by the Invention

The problem to be solved by the present invention is to provide a material (an anti-adhesion material) that exerts an anti-adhesion effect when applied to the surgical site and a material (a substitute biomembrane) that substitutes the biological function when applied to defective part after surgery.

The problem to be solved by the present invention is also to provide an anti-adhesion material that has high membrane strength to allow for suture, can reduce postoperative adhesion of the living tissue, and has excellent biocompatibility.

Means for Solving the Problems

The present inventors have earnestly studied and as a result have found that the problems as mentioned above could be solved by using decellularized tissues from biological tissues as an anti-adhesion material to thereby complete the present invention. Thus, the present invention relates to an anti-adhesion material wherein a biocompatible polymer is complexed to decellularized tissues prepared by decellularizing biological tissues.

The present inventors have also found that a substitute biomembrane and an anti-adhesion material prepared by complexing fibrin glue with decellularized tissues become a tissue substitute or a barrier when applied to defective part or between tissues so as to prevent adhesion to the surrounding tissues to thereby complete the present invention.

Thus, the present invention includes:
(1) an anti-adhesion material comprising decellularized tissues and a biocompatible polymer;
(2) a method for preparing an anti-adhesion material comprising complexing a biocompatible polymer to decellularized tissues;
(3) an anti-adhesion material kit comprising decellularized tissues and a biocompatible polymer;
(4) a substitute biomembrane comprising decellularized tissues and a biocompatible polymer;
(5) a method for preparing a substitute biomembrane comprising complexing a biocompatible polymer to decellularized tissues;
(6) a substitute biomembrane kit comprising decellularized tissues and a biocompatible polymer.

Specifically, the present invention includes the followings:

[1] An anti-adhesion material comprising decellularized tissues and a biocompatible polymer;
[2] The anti-adhesion material of [1] above wherein the decellularized tissues are the ones prepared by decellularizing biological tissues selected from the group consisting of pericardium, bladder, amnion, dura mater, peritoneum, diaphragm, fascia, small intestine submucosa and skin;
[3] The anti-adhesion material of [1] or [2] above wherein the decellularized tissues are the ones prepared by treating biological tissues with a high hydrostatic pressure or with a surfactant;
[4] The anti-adhesion material of [3] above wherein the treatment with a high hydrostatic pressure comprises applying a hydrostatic pressure of 50 to 1,500 MPa to biological tissues in a medium;

[5] The anti-adhesion material of any one of [1] to [4] above wherein the biocompatible polymer is a biocompatible polymer which naturally occurs;
[6] The anti-adhesion material of any one of [1] to [5] above wherein the biocompatible polymer is fibrin glue;
[7] The anti-adhesion material of any one of [1] to [6] above wherein the biocompatible polymer is complexed to the decellularized tissues;
[8] The anti-adhesion material of [7] above wherein the complexation of the biocompatible polymer to the decellularized tissues is immersion or coating of the biocompatible polymer to the decellularized tissues;
[9] The anti-adhesion material of any one of [1] to [8] above wherein the anti-adhesion material is an anti-adhesion membrane and a film thickness is 10 to 5,000 μm;
[10] A method for preparing an anti-adhesion material comprising complexing a biocompatible polymer to decellularized tissues;
[11] The method of [10] above wherein the complexation is immersion or coating of the biocompatible polymer to the decellularized tissues;
[12] An anti-adhesion material kit comprising decellularized tissues and a biocompatible polymer;
[13] The kit of [12] above wherein the decellularized tissues are the ones prepared by decellularizing biological tissues selected from the group consisting of pericardium, bladder, amnion, dura mater, peritoneum, diaphragm, fascia, small intestine submucosa and skin;
[14] The kit of [12] or [13] above wherein the decellularized tissues are the ones prepared by treating biological tissues with a high hydrostatic pressure or with a surfactant;
[15] The kit of [14] above wherein the treatment with a high hydrostatic pressure comprises applying a hydrostatic pressure of 50 to 1,500 MPa to biological tissues in a medium;
[16] The kit of any one of [12] to [15] above wherein the biocompatible polymer is fibrin glue;
[17] The kit of any one of [12] to [16] above wherein the biocompatible polymer is complexed to the decellularized tissues;
[18] The kit of [17] above wherein the complexation of the biocompatible polymer to the decellularized tissues is immersion or coating of the biocompatible polymer to the decellularized tissues;
[19] The kit of any one of [12] to [18] above wherein the anti-adhesion material is an anti-adhesion membrane and a film thickness is 10 to 5,000 μm;
[20] A substitute biomembrane comprising decellularized tissues and a biocompatible polymer;
[21] The substitute biomembrane of [20] above wherein the decellularized tissues are the ones prepared by decellularizing biological tissues selected from the group consisting of pericardium, bladder, amnion, dura mater, peritoneum, diaphragm, fascia, small intestine submucosa and skin;
[22] The substitute biomembrane of [20] or [21] above wherein the decellularized tissues are the ones prepared by treating biological tissues with a high hydrostatic pressure or with a surfactant;
[23] The substitute biomembrane of [22] above wherein the treatment with a high hydrostatic pressure comprises applying a hydrostatic pressure of 50 to 1,500 MPa to biological tissues in a medium;
[24] The substitute biomembrane of any one of [20] to [23] above wherein the biocompatible polymer is a biocompatible polymer which naturally occurs;
[25] The substitute biomembrane of any one of [20] to [23] above wherein the biocompatible polymer is fibrin glue;
[26] The substitute biomembrane of any one of [20] to [25] above wherein the biocompatible polymer is complexed to the decellularized tissues;
[27] The substitute biomembrane of [26] above wherein the complexation of the biocompatible polymer to the decellularized tissues is immersion or coating of the biocompatible polymer to the decellularized tissues;
[28] The kit of any one of [20] to [27] above wherein a film thickness is 10 to 5,000 μm;
[29] A method for preparing a substitute biomembrane comprising complexing a biocompatible polymer to decellularized tissues;
[30] The method of [29] above wherein the complexation is immersion or coating of the biocompatible polymer to the decellularized tissues;
[31] A substitute biomembrane kit comprising decellularized tissues and a biocompatible polymer;
[32] The kit of [31] above wherein the decellularized tissues are the ones prepared by decellularizing biological tissues selected from the group consisting of pericardium, bladder, amnion, dura mater, peritoneum, diaphragm, fascia, small intestine submucosa and skin;
[33] The kit of [31] or [32] above wherein the decellularized tissues are the ones prepared by treating biological tissues with a high hydrostatic pressure or with a surfactant;
[34] The kit of [33] above wherein the treatment with a high hydrostatic pressure comprises applying a hydrostatic pressure of 50 to 1,500 MPa to biological tissues in a medium;
[35] The kit of any one of [31] to [34] above wherein the biocompatible polymer is fibrin glue;
[36] The kit any one of [31] to [35] above wherein the biocompatible polymer is complexed to the decellularized tissues;
[37] The kit of [36] above wherein the complexation of the biocompatible polymer to the decellularized tissues is immersion or coating of the biocompatible polymer to the decellularized tissues; and
[38] The kit of any one of [31] to [37] above wherein a film thickness of the substitute biomembrane is 10 to 5,000 μm.

Effects of the Invention

The substitute biomembrane or the anti-adhesion material of the present invention has an effect of acting as a substitute of defected tissues when applied to defective part of tissues or an effect of preventing adhesion to tissues in contact with the applied part.

By using the anti-adhesion material of the present invention, adhesion can drastically be reduced. Also, the substitute biomembrane or the anti-adhesion material of the present invention has sufficient strength for suture to tissues to allow for their fixation to tissues.

BEST MODE FOR CARRYING OUT THE INVENTION

The present invention includes a substitute biomembrane comprising decellularized tissues and a biocompatible polymer. The present invention also includes an anti-adhesion material comprising decellularized tissues and a biocompatible polymer.

The anti-adhesion material of the present invention is characterized by that decellularized tissues prepared by decellularizing biological tissues and a biocompatible polymer are complexed to each other. As used herein, the term "complexation" denotes the conditions where a biocompatible polymer is not easily detached from decellularized tissues. Decellularized tissues and a biocompatible polymer may chemically be bound to each other, or a biocompatible polymer may physically be adsorbed to decellularized tissues, or a biocompatible polymer may be immersed to decellularized tissues. An example of physical adsorption is coating. In accordance with the present invention, immersion or coating of a biocompatible polymer to decellularized tissues is preferable.

1. Decellularized Tissues

For the anti-adhesion material of the present invention, decellularized tissues in the form of sheet are used. Biological tissues to be used for decellularized tissues and the location from which biological tissues are obtained are not particularly limited as far as they are from vertebrates and are of such a size and a thickness that can be used for the anti-adhesion material.

The decellularized tissues can be obtained by collecting biological tissues from vertebrates (donners) and subjecting the biological tissues to decellularization treatment. The biological tissues are decellularized to remove donner-derived cells and pathogens (viruses and bacteria). Thus, even if the decellularized biological tissues are transplanted to animals different from the donners, a heterologous immune reaction is restrained. Therefore, the kind of animals from which biological tissues are collected is not particularly limited. On the other hand, since biological tissues are preferably readily available, they are preferably collected from an animal other than human, preferably domestic animals of mammals or domestic animals of birds. The domestic animals of mammals include cattle, horses, camels, llama, donkey, yak, sheep, pigs, goats, deer, alpacas, dogs, raccoon dogs, weasels, foxes, cats, rabbits, hamsters, guinea pigs, rats, squirrels, raccoons, and the like. The domestic animals of birds include parakeet, parrot, chicken, ducks, turkeys, geese, guinea fowl, pheasant, ostrich, emu, quail, and the like. Among these, biological tissues from pigs, rabbits or cattle are preferable in view of stable availability.

The biological tissues include tissues which have an extracellular matrix structure and which can be decellularized, the tissues being selected from the group consisting of liver, kidney, ureter, bladder, urethra, tongue, tonsils, esophagus, stomach, diaphragm, small intestine, large intestine, peritoneum, anus, pancreas, heart, pericardium, blood vessels, spleen, lung, brain, dura mater, bone, spinal cord, cartilage, testis, amnion, uterus, fallopian tube, ovary, placenta, cornea, skeletal muscle, tendons, nerves, skin, and the like. In case that the decellularized tissues are in the form of sheet, as being easily applied to the living body, the preferable tissues include those selected from the group consisting of pericardium, bladder, amnion, dura mater, peritoneum (Greater omentum, Lesser omentum), diaphragm, submucosa (e.g. small intestine submucosal tissue) and skin. The tissues which can be decellularized include tissues not in the form of sheet as can easily be applied to the living body if they are processed into sheet. More preferably, the tissues are skin, pericardium and amnion. Skin normally consists of epidermis, dermis, subcutaneous tissue, and the like. For the anti-adhesion material of the present invention, single use of dermis is preferable.

For collection of biological tissues from animals, methods suitable for the kind of animal donners or tissues from the living body may be used. The biological tissues collected from animals are subject to decellularization treatment. Decellularization treatment is not particularly limited as far as it can remove donner-derived cells and pathogens and includes treatment with a surfactant (Singelyn J. M., et al., Biomaterials, 2009, 30, 5409-5416; Singelyn J. M, et al., J. Am. Coll. Cardiol., 2012, 59, 751-763; Sonya B., et al., Sci. Transl. Med., 2013, 5, 173ra25), enzyme treatment, osmotic pressure treatment, freeze and thawing, treatment with an oxidizing agent, treatment with a high hydrostatic pressure (Sasaki S., et al., Mol. Vis., 2009, 15, 2022-2028; Yoshihide H., et a Biomaterials, 2010, 31, 3941-3949; Seiichi F., et al., Biomaterials, 2010, 31, 3590-3595; Negishi J., et al., J. Artif. Organs, 2011, 14, 223-231; Japan Patent No. 4092397; Japanese Patent Publication No. 2008-111530; Japanese Patent Publication No. 2009-50297) and a combination thereof, which may suitably be selected depending on the kind of animal donners and biological tissues. Treatment with a high hydrostatic pressure is particularly preferable in view of no use during decellularization of chemicals that may affect adversely to the human body since it destroys donner-derived cells and pathogens by applying hydrostatic pressure to biological tissues in a medium. On the other hand, even when decellularization treatment is done with chemicals, chemicals can be removed by sufficiently washing the tissues after decellularization treatment.

Decellularization treatment may include a step of washing decellularized biological tissues. A method for washing decellularized biological tissues may suitably be selected depending on the kind of decellularization treatment. A method for washing includes immersing in a washing solution (Japanese Patent Publication No. 2010-227246) and irradiation of microwave (Japan Patent No. 4189484).

A pressure at which treatment with a high hydrostatic pressure is done may be any pressure with which donner-derived cells and pathogens are destroyed and is suitably selected depending on the kind of animal donners and the kind of biological tissues. For a hydrostatic pressure, 2 to 1,500 MPa is exemplified. When a hydrostatic pressure applied is more than 50 MPa, decellularization of biological tissues is accomplished sufficiently. Therefore, a hydrostatic pressure is preferably 50 to 1,500 MPa, more preferably 80 to 1,300 MPa, even more preferably 90 to 1,200 MPa, and most preferably, 95 to 1,100 MPa.

A medium used for application of a hydrostatic pressure includes water, a saline, propylene glycol or an aqueous solution thereof, glycerol or an aqueous solution thereof, an aqueous sugar solution, and the like. A buffer includes acetate buffer, phosphate buffer, citrate buffer, borate buffer, tartrate buffer, Tris buffer, HEPES buffer, MES buffer, and the like. A sugar for an aqueous sugar solution includes erythrose, xylose, arabinose, allose, talose, glucose, mannose, galactose, erythritol, xylitol, mannitol, sorbitol, galactitol, sucrose, lactose, maltose, trehalose, dextran, alginic acid, hyaluronic acid, and the like.

A temperature at which treatment with a high hydrostatic pressure is done is not particularly limited and may be any temperature at which ice is not formed and tissues are not damaged by heat. In view of smooth decellularization and few damages to tissues, a temperature is preferably 0° C. to 45° C., more preferably 4° C. to 40° C., even more preferably 10° C. to 37° C., and most preferably 15° C. to 35° C.

An interval of time for treatment with a high hydrostatic pressure is preferably 5 to 60 minutes, and more preferably 7 to 30 minutes since with too short interval of time decellularization treatment is not sufficiently done whereas too long interval of time leads to waste of energy.

Presence or absence of decellularization may be confirmed by histologic stain (hematoxylin-eosin stain) or quantitation of the remaining DNAs.

After application of a high hydrostatic pressure to biological tissues, cells within the biological tissues are destroyed and are removed with a washing solution. A washing solution may be the same as, or different from, a medium used for application of a high hydrostatic pressure and may be a combination of plural kinds of a washing solution. A washing solution preferably contains a nuclease, an organic solvent or a chelating agent. A nuclease and an organic solvent can improve efficiency of removal of nucleic acids and lipids, respectively, from biological tissues to which a hydrostatic pressure is applied. A chelating agent can inactivate calcium ions and magnesium ions in decellularized tissues to thereby prevent calcification which may occur when decellularized tissues are applied to affected portions.

An organic solvent is preferably a water-soluble organic solvent as having a high effect of lipid removal. Preferred are ethanol, isopropanol, acetone and dimethyl sulfoxide. A chelating agent includes imino carboxylic acid chelating agent such as ethylenediaminetetraacetic acid (EDTA), nitrilotriacetic acid (NTA), diethylenetriamine pentaacetic acid (DTPA), hydroxyethyl ethylenediaminetriacetic acid (HEDTA), triethylene-tetraamine hexaacetic acid (TTHA), 1,3-propane diamine tetraacetic acid (PDTA), 1,3-diamino-2-hydroxy propane tetraacetic acid (DPTA-OH), hydroxyethyl imino diacetic acid (HIDA), dihydroxyethyl glycine (DHEG), glycol ether diamine tetraacetic acid (GEDTA), dicarboxymethyl glutamic acid (CMGA), 3-hydroxy-2,2'-imino disuccinic acid (HIDA) and carboxymethyl aspartic acid (ASDA), or a salt thereof; hydroxycarboxylic acid chelating agent such as citric acid, tartaric acid, malic acid and lactic acid, or a salt thereof. A salt of a chelating agent includes sodium salt or potassium salt.

Next, tissues after decellularization treatment are preferably lyophilized in view of maintenance of stability. The conditions for lyophilization may be any as far as water is removed from the tissues after decellularization and may suitably be selected depending on the kind of biological tissues. The conditions include program freezing used for cryopreservation of homeotransplant (−1° C./min., 90 min. or more) and lyophilization with a vacuum drying apparatus.

In view of high efficiency of washing, a washing solution may contain a surfactant. A surfactant includes an anionic surfactant such as fatty acid soap, alkoxycarboxylate, polyoxyethylene alkoxycarboxylate, alkyl sulfonate, alkyl benzene sulfonate, alkylsulfuric acid ester salt, polyoxyethylene alkylsulfuric acid ester salt, alkylphosphonate ester salt, α-sulfo fatty acid ester salt, N-acyl glutamate, acyl-N-methyl taurine salt, N-alkyl sarcosine salt, cholate and deoxycholate;

a cationic surfactant such as alkyl dimethylamine, alkyl diethanolamine, alkyl trimethyl ammonium salt, dialkyl dimethyl ammonium salt, alkylpyridinium salt and alkyl benzyl dimethyl ammonium salt;

an ampholytic surfactant such as alkyl dimethylamine oxide, alkylcarboxybetaine, alkylamidepropylbetaine, alkylamidepropylsulfobetaine, alkylimidazoliumbetaine, 3-[(3-cholamidopropyl)dimethylammonio]-2-Hydroxy-1-propanesulfonate (CHAPSO), and 3-[(3-cholamidepropyl)dimethylammonio]-1-propanesulfonate (CHAPS);

nonionic surfactant such as fatty acid ester of glycerin, sorbitan fatty acid ester, sucrose fatty acid ester, trehalose fatty acid ester, polyethylene glycol fatty acid ester, polyoxyethylene fatty acid ester of glycerin, polyoxyethylene sorbitan fatty acid ester, polyoxyethylene alkyl ether, polyoxyethylene alkylphenyl ether, polyoxyethylene polyoxypropylene ether, alkyl(poly)glycerin ether, fatty acid alkanolamide, polyoxyethylene fatty acid alkanolamide, alkyl (poly)glycoside, alkyl maltoside, alkyl thioglucoside, alkylmaltopyranoside, alkanoyl-N-methyl-D-glucosamine, N,N-bis(3-D-gluconamidopropyl)cholamide (BIGCHAP) and N,N-bis(3-D-gluconamidopropyl)deoxycholamide (deoxy-BIGCHAP).

In view of removal of cells, surfactant is preferably alkyl sulfonate, alkylsulfuric acid ester salt, polyoxyethylene alkylsulfuric acid ester salt, α-sulfofatty acid ester salt, polyoxyethylene alkyl ether, polyoxyethylene alkyl phenyl ether and alkyl(poly)glycoside and more preferably alkyl sulfonate, polyoxyethylene alkyl ether, polyoxyethylene alkyl phenyl ether and alkyl(poly)glycoside.

A temperature at which biological tissues to which a high hydrostatic pressure was applied is washed is not particularly limited and may be any temperature at which tissues are not damaged by heat. In view of good washing and few effects on tissues, a temperature is preferably 0° C. to 45° C., more preferably 1° C. to 40° C., and most preferably 2° C. to 35° C. When washing, a washing solution may be shaken or stirred as appropriate.

2. Biocompatible Polymer

As used herein, a biocompatible polymer denotes a polymer which does not exert deleterious effects when applied to the living body and has hydrophilicity. Specifically, a biocompatible polymer denotes a polymer which has (i) a weight-average molecular weight of 500 or more, (ii) 2,000 mg/kg or more of LD50 when orally administered to rats and (iii) solubility or extended wettability to water. As used herein, a weight-average molecular weight is the one calculated with gel permeation chromatography (also referred to as "GPC"), polystyrene equivalent of a weight-average molecular weight when GPC is measured with tetrahydrofuran as a solvent or pullulan equivalent of a weight-average molecular weight when GPC is measured with water as a solvent. In case that a biocompatible polymer is complexed by immersion or physical adsorption, complexation is often insufficient when a weight-average molecular weight of a biocompatible polymer is low and therefore a weight-average molecular weight of a biocompatible polymer is preferably 1,000 or more and more preferably 2,000 or more.

A biocompatible polymer is roughly classified into a naturally occurring biocompatible polymer, a biocompatible polymer which is processed from a naturally occurring biocompatible polymer and an artificially synthesized biocompatible polymer. Among biocompatible polymers, a naturally occurring biocompatible polymer or a biocompatible polymer which is processed from a naturally occurring biocompatible polymer, for instance, polysaccharides such as chondroitin sulfate, dermatan, heparin, heparan, alginic acid, hyaluronic acid, dermatan sulfate, keratan sulfate, chitin chitosan, pectin, amylose amylopectin, glycogen, dextrin, dextran and β-1,3-glucan, or a salt thereof; polysaccharide derivatives such as methyl cellulose, hydroxyethyl cellulose, hydroxypropyl cellulose, carboxymethyl cellulose, cellulose acetate and carboxymethyl chitosan, and a salt thereof; polypeptides or glycoproteins such as collagen, gelatin, elastin, fibrinogen, fibrin or fibrin glue, fibronectin, laminin, vitronectin, entactin, thrombospondin, tenacin, casein, avidin, cadherin, mucin and proteoglycan.

Among biocompatible polymers, an artificially synthesized biocompatible polymer includes, for instance, synthetic polypeptides such as polyalanine, polyasparagine, polyaspartic acid, polyarginine, polyisoleucine, polyornithine, polyglycine, polyglutamic acid, polytryptophan, polytyrosine, polyhistidine, polyproline and polylysine, or a salt thereof; poly-(hydroxycarboxylic acids) such as polyglycolic acid, polylactic acid, polyhydroxybutyric acid, poly ε-caprolactone and polytartaric acid; polyol ethers such as Polyethylene glycol and polyglycerin; radically polymerized polymers such as poly(meth)acrylic acid, polyacrylamide, polyfumaric acid, poly(meth)acrylate containing phosphoryl-choline group, polyhydroxyethyl(meth)-acrylate and poly-(diallyidimethylammonium), and a salt thereof.

Among biocompatible polymers, a bioabsorbable polymer is preferable in view of lesser burden of patients as being absorbed in the living body after operation. A bioabsorbable polymer includes a biocompatible polymer which naturally occurs, a biocompatible polymer which naturally occurs and is processed, synthetic polypeptides or a salt thereof and poly(hydroxycarboxylic acids) and is preferably a biocompatible polymer which naturally occurs in view of absorbability into the body, more preferably polysaccharides or a salt thereof, polypeptides or glycoproteins in view of prevention of adhesion, and even more preferably alginic acid, hyaluronic acid and fibrin glue.

3. Fibrin Glue

Fibrin glue is a formulation wherein pasty coagulum, which is formed by the reaction of the enzyme thrombin to fibrinogen, is utilized for tissue sealing, adhesion of damaged portions of organs, hemostasis and the like. The kind of fibrin glue is not particularly limited and its constituents such as fibrinogen and thrombin may be derived from blood or may be prepared by recombinant technique. Fibrin glue preferably includes Bolheal (manufactured by CHEMO-SERO-THERAPEUTIC RESEARCH INSTITUTE) which consists of lyophilized powder of fibrinogen, a fibrinogen solvent, lyophilized powder of thrombin and a thrombin solvent.

4. Complexation

Complexation of decellularized tissues and a biocompatible polymer includes formation of chemical bond between decellularized tissues and a biocompatible polymer, physical adsorption of a biocompatible polymer to decellularized tissues, immersion of a biocompatible polymer to decellularized tissues, and the like. Among these, immersion of a biocompatible polymer to decellularized tissues is preferable since the effect of a biocompatible polymer persists for a long period of time. For physical adsorption of a biocompatible polymer to decellularized tissues, a biocompatible polymer may be attached or coated to decellularized tissues. For immersion of a biocompatible polymer to decellularized tissues, decellularized tissues may be immersed into a solution containing a biocompatible polymer. In view of higher efficiency of immersion, decellularized tissues are preferably immersed after lyophilization and more preferably the pressure is applied or reduced while immersion (WO 2013/ 032009).

In case that a film thickness of an anti-adhesion material is too thin, insufficient membrane strength is sometimes obtained. In case that a film thickness of an anti-adhesion material is too thick, an anti-adhesion material is less likely attached to uneven affected portions to give a feeling of incongruity. Therefore, a film thickness of an anti-adhesion material is preferably 10 to 5,000 μm, more preferably 30 to 2,000 μm, and most preferably 50 to 1,000 μm.

The anti-adhesion material of the present invention is suitably used for prevention of adhesion at the time of surgery. For instance, the anti-adhesion material of the present invention is used for preventing adhesion of the surface of biological tissues injured at chest surgery, abdominal surgery and endoscopic surgery to diseases in bronchus, lung, heart, liver, spleen, pancreas, kidney, uterus, ovary, and the like; suture surgery of Achilles tendon, tendon of the hand, nerves, and the like; suture after Cesarean delivery. The anti-adhesion material of the present invention is used by attaching it to tissues liable to adhesion but may also be sutured to tissues as needed. Also, when applied to defective tissue, the anti-adhesion material of the present invention may suitably be used as a substitute biomembrane so as to prevent adhesion of tissues in contact with part to which the anti-adhesion material is applied and to function as substitute of histological defect.

In case that decellularized tissues and fibrin glue are complexed to each other, a method of coating fibrin glue to decellularized tissues, a method of dispersing powder of active ingredients of fibrin glue (fibrinogen powder, thrombin powder) to decellularized tissues, and a method of immersing fibrinogen to decellularized tissues and then acting thrombin thereto are exemplified. In case of coating, coating of fibrin glue to at least one side of decellularized tissues is exemplified. Namely, coating of fibrin glue to one side or both sides of decellularized tissues is exemplified. A side for coating is preferably a side conceivable of contact or adhesion with tissues after coating. For instance, in case of coating to defect of pericardium, coating of fibrin glue to the side in contact with epicardium in view of prevention of adhesion to epicardium, coating of fibrin glue to the side in contact with pleura in view of prevention of adhesion to pleura, or coating of fibrin glue to both of the sides are exemplified. For coating, either of fibrinogen or thrombin may be first coated and then the other may be coated or both of fibrinogen and thrombin may be coated simultaneously. Spray coating with a spray apparatus may also be employed. An area of decellularized tissues to which fibrin glue is coated may be a partial area of decellularized tissues or a whole area of decellularized tissues. In case that an anti-adhesion effect is to be exerted throughout decellularized tissues, coating to a whole area of decellularized tissues is preferable. For coating, the constituents of fibrin glue may be coated on the surface of decellularized tissues or may be immersed into decellularized tissues. Preferably, the constituents of fibrin glue are coated on the surface of decellularized tissues and also immersed into decellularized tissues.

Each concentration of thrombin and fibrinogen in case that fibrin glue is applied to decellularized tissues is not particularly limited as far as it can form gel by fibrin glue on the surface of decellularized tissues. For instance, 4 mg/mL to 250 mg/mL is exemplified in case of fibrinogen and 1 U/mL to 1,200 U/mL is exemplified in case of thrombin.

Application site is not particularly limited as far as it is a site that has cellular tissues or it is of tissues liable to adhesion. Application site may be the same tissues as original biological tissues or different tissues from original biological tissues. For instance, it includes pericardium, heart, epicardium, pleura, abdominal wall, peritoneum, bladder, amnion, uterus, dura mater, diaphragm, small intestine, large intestine, stomach, anus, pancreas, spleen, liver, kidney, lung, skin, esophagus, ligament and tendon. Preferably, it is pericardium and abdominal wall.

The present invention includes a substitute biomembrane kit or an anti-adhesion material kit wherein decellularized tissues and a biocompatible polymer are separately formulated. The kit may be used such that, when using, an operator combines decellularized tissues and a biocompatible polymer to complex them and applies the complexation to affected portions. In case that decellularized tissues are lyophilized, the decellularized tissues may be immersed with a solvent and, after restoration, the decellularized tissues may be applied to affected portions and a biocompatible polymer may be coated thereto. Thus, the kit may comprise a solvent for restoration. In case that the kit comprises fibrin glue, restoration may be carried out with a fibrinogen solution or a thrombin solution. The kit may also be composed of decellularized tissues to which either fibrinogen thrombin is complexed and a formulation of the other. In that case, coating of the complexed decellularized tissues to affected portions and subsequent application of a formulation of the other are exemplified. For instance, in case of a kit composed of decellularized tissues to which fibrinogen is complexed and a thrombin formulation, the decellularized tissues may be applied and then the thrombin formulation may be applied.

EXAMPLES

The present invention is explained in more detail by means of the following Examples but is not limited thereto. Unless otherwise mentioned, "portion" and "%" referred to in the Examples are based on a mass scale.
[Decellularized Tissues]
The dermic layer was separated from the porcine skin to obtain sheet dermis (a film thickness: 400 μm). A bag with the zipper made of polyethylene was charged with the dermis and a saline as a medium for a high hydrostatic pressure treatment and, using High Pressure Processing Equipment for R&D (manufactured by Kobe Steel, Ltd.; trade name: Dr. Chef), a hydrostatic pressure of 1,000 MPa was applied for 15 minutes. The dermis after a high hydrostatic pressure treatment was washed by shaking in a saline containing DNase as a nuclease at 20 ppm at 4° C. for 96 hours. The dermis was further shaken in 80% ethanol at 4° C. for 72 hours and then in a saline at 4° C. for 2 hours to give decellularized tissue in a sheet (hereinafter referred to as "wet sheet"). A wet sheet and a lyophilized wet sheet (hereinafter referred to as "lyophilized sheet") were used for a test.

Example 1

A lyophilized sheet was immersed in 2% saline solution of sodium alginate at room temperature for 2 hours to give an anti-adhesion membrane of Example 1.

Example 2

A lyophilized sheet was immersed in 40% saline solution of polyethylene glycol 4000 at room temperature for 2 hours to give an anti-adhesion membrane of Example 2.

Example 3

A lyophilized sheet was immersed in 10% saline solution of gelatin at room temperature for 2 hours to give an anti-adhesion membrane of Example 3.

Comparative Example 1

A wet sheet was set as an anti-adhesion membrane of Comparative Example 1.

Comparative Example 2

In accordance with the Examples of JP 2013-226166, an aqueous solution of 2.7 mass % of gelatin powder (manufactured by Nippi, Incorporated; trade name: MediGelatin) was coated to glass plate, which was air dried and heated in a vacuum oven at 140° C. for 10 hours for thermal cross-linking to give an anti-adhesion membrane of Comparative Example 2 with a film thickness of 100 μm.

Comparative Example 3

In accordance with Example 1 of JP 2000-116765, an aqueous solution of 1 mass % of sodium hyaluronate was coated to glass plate and thereto an aqueous solution containing 1 mass % of chitosan and 0.6 mass % of acetic acid was further coated. The glass plate was then air dried to give an anti-adhesion membrane of Comparative Example 2 with a film thickness of 150 μm.

Comparative Example 4

In accordance with Example 1 of JP 2010-284216, rayon non-woven fabric was carboxymethylated with monochloroacetic acid (degree of etherification: 0.84, weight molecular weight: 160,000) and coated to glass plate. An aqueous solution of 1 mass % of sodium hyaluronate was coated to glass plate and thereto an aqueous solution containing 1 mass % of chitosan and 0.6 mass % of acetic acid was further coated. The glass plate was then air dried to give a sheet. The sheet was immersed in a methanol solution of 4% hydrochloric acid (moisture content 10%) at 25° C. for 6 hours. Thereafter, the sheet was washed with 50% aqueous methanol solution, 80% aqueous methanol solution and 100% aqueous methanol solution sequentially and dried to give an anti-adhesion membrane of Comparative Example 4 with a film thickness of 300 μm.
1. Assessment of Suture Strength
Wistar rats (male, 6-12 weeks old) were anesthetized. The abdomen was shaved and the skin was disinfected with a povidone-iodine solution (trade name: Isodine). The ventral region was incised with sterile scalpel to create two skin pockets of 15 mm in length and mm in width on the left and right. The tunica muscularis and the peritoneum under the skin pockets were removed in a square having a length of 10 mm and a width of 10 mm. The exposed organ surface was abraded with sterile gauze to cause damage to the organ. To the removal site of the right side of the abdomen was sutured the anti-adhesion membrane with surgical suture (Johnson & Johnson K.K.; trade name: Ethicon 6-0 PROLENE). In case that suture was not possible due to lack of strength, the anti-adhesion membrane was merely attached to the removal site without suture. As a control, to the removal site of the left side of the abdomen was sutured the peritoneum without using the anti-adhesion membrane. Thereafter, the incision layer was sutured with surgical suture. Suture strength of the anti-adhesion membrane was assessed based on the following criteria. The results are shown in Table 1.
○: Having strength and being capable of suture to peritoneum
x: Having insufficient strength and being incapable of suture to peritoneum 2. Assessment of Anti-Adhesion Effect The rats subject to surgery were bred for 7 days and then abdominal surgery was performed to remove the surgical area. Anti-adhesion effect with regard to adhesion between the liver or the small intestine and the anti-adhesion membrane or the peritoneum was assessed based on the following criteria. The results are shown in Table 1.

5: Utterly no state of adhesion was observed with extremely good anti-adhesion effect
4: Only state of adhesion that is thin and easily dissected was observed with good anti-adhesion effect
3: State of adhesion requiring light traction in a narrow range at one site was observed with slightly bad anti-adhesion effect
2: State of adhesion requiring somewhat traction at one site or adhesion requiring light traction at two or three sites was observed with bad anti-adhesion effect
1: State of adhesion requiring somewhat traction at two or more sites or adhesion requiring light traction at four or more sites was observed with extremely bad anti-adhesion effect
0: Strong State of adhesion was observed with no anti-adhesion effect

TABLE 1

|  | Suture strength of anti-adhesion membrane | Anti-adhesion effect of anti-adhesion membrane | Anti-adhesion effect of control |
| --- | --- | --- | --- |
| Ex. 1 | ○ | 5 | 1 |
| Ex. 2 | ○ | 5 | 0 |
| Ex. 3 | ○ | 4 | 1 |
| Comp. Ex. 1 | ○ | 2 | 1 |
| Comp. Ex. 2 | × | 2 | 0 |
| Comp. Ex. 3 | × | 3 | 1 |
| Comp. Ex. 4 | × | 2 | 1 |

From the results shown in Table 1, it is understood that the anti-adhesion membrane of the present invention has strength to such an extent that enables suture and excellent anti-adhesion effect.

Example 4

1. Preparation of Decellularized Pericardium

Decellularized porcine pericardium was prepared by a method of a high hydrostatic pressure or treatment with a surfactant. For a method of a high hydrostatic pressure, a polyethylene bag was charged with porcine pericardium together with a saline and sealed. Using Dr. Chef (manufactured by Kobe Steel, Ltd.), treatment with a high hydrostatic pressure of 3,000 to 10,000 atm was performed. Treatment with a surfactant was conducted using 0.05% SDS (Sodium Dodecyl Sulfate; manufactured by Wako Pure Chemical Industries, Ltd.; ionic surfactant), 0.5% SDS, 0.5% CHAPS (3-[(3-Cholamidopropyl)dimethylammonio]-1-propanesulfonate; manufactured by DOJINDO; ampholytic surfactant), or 1% Triton X-100 (manufactured by Sigma; nonionic surfactant). The porcine pericardium treated with a high hydrostatic pressure or with a surfactant was washed with a washing solution containing a nuclease and a washing solution containing alcohol. However, the porcine pericardium treated with 0.5% SDS was not treated with a washing solution containing a nuclease. After washing, the decellularized porcine pericardium was incised to the size of 15 mm×15 mm. The incised pericardium was lyophilized under reduced pressure for more than 24 hours using a vacuum drying apparatus (EYELA).

2. Experiment with Rat Heart Adhesion Model

Wistar rats (male, 10-12 weeks old) were anesthetized by intramuscular injection of 0.1 ml Somnobentyl. The side chest was shaved and disinfected with Isodine. The trachea of the anesthetized rats were intubated and connected to a ventilator. The rats were laid at recumbent position, the side chest was incised and tunica muscularis and pericardium were removed. The surface of the heart was abraded with non-woven fabric to induce inflammation. The heart was covered with each of the anti-adhesion materials, the incised part of the rats was sutured and extubation was carried out after spontaneous breathing was stabilized.

3. Group Constitution and Observation

Fibrin glue was coated to both sides of the dried decellularized porcine pericardium to prepare anti-adhesion materials. Fibrin glue was prepared by mixing 80 mg/mL of a fibrinogen solution and 250 U/mL of a thrombin solution using a coating applicator. A fibrinogen solution was prepared using lyophilized powder of fibrinogen contained in Bolheal (trade mark; manufactured by THE CHEMO-SERO-THERAPEUTIC RESEARCH INSTITUTE) and a fibrinogen solvent. A thrombin solution was prepared using lyophilized powder of thrombin contained in Bolheal and a thrombin solvent.

As a control, (1) Group with no application of the anti-adhesion materials was studied. Also, (2) Group with coating of Bolheal to abraded part of heart, and (3) Group with immersion of dried decellularized porcine pericardium in saline were used. As an observation period, the experiment was performed in two groups (1 week and 4 weeks). The rats were euthanized and the chest was incised to assess findings as to adhesion. Also, (4) the anti-adhesion materials and the heart were assessed histologically by HE stain.

4. Results

Figure 1:
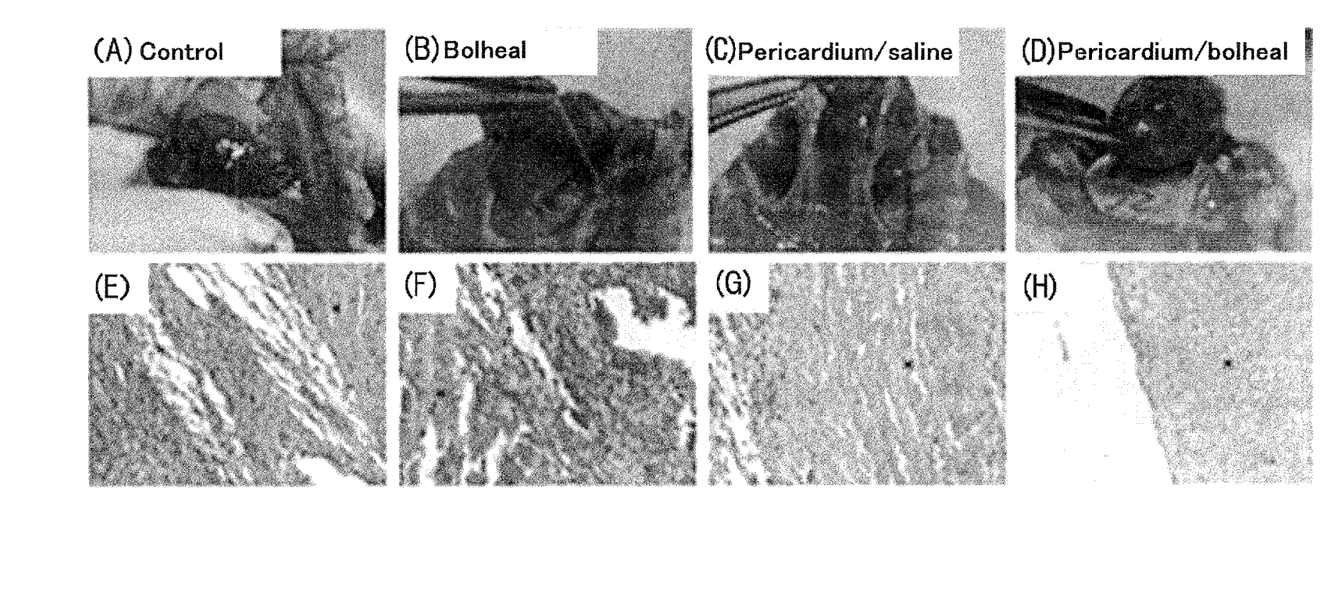
FIG. 1 shows assessment on Day 7 after applying the anti-adhesion material of the present invention to rat model of heart adhesion in which E and F show the myocardium tissue whereas G and H show the pericardium, respectively.

In Group with no application of the anti-adhesion materials, severe adhesion was observed between the heart and the chest walls. In case of Group with coating of Bolheal and Group with immersion of dried decellularized porcine pericardium in saline, state of adhesion equal to that of control was observed. In case of Group with application of the anti-adhesion materials, state of adhesion was scarcely observed around the heart and only minor state of adhesion was observed in several cases. As shown in HE stain on Day 7 (FIG. 1), in case of Group with application of anti-adhesion material, almost no inflammation was observed and cellular infiltration into the decellularized tissues was observed to reveal that the anti-adhesion material of the present invention has an excellent anti-adhesion effect and is useful as a substitute biomembrane with high biocompatibility.

(1) Group with no application of the anti-adhesion materials: severe adhesion was observed (n=5).
(2) Group with coating of Bolheal: severe adhesion was observed (n=5).
(3) Group with immersion of dried decellularized porcine pericardium in saline: severe adhesion was observed (n=5).
(4) Group with application of anti-adhesion material (a high hydrostatic pressure treatment): state of adhesion was scarcely observed (n=5).
(5) Group with application of anti-adhesion material (treatment with 0.05% SDS surfactant): state of adhesion was scarcely observed (n=4).
(6) Group with application of anti-adhesion material (treatment with 0.5% SDS surfactant): state of adhesion was scarcely observed (n=5).

(7) Group with application of anti-adhesion material (treatment with 0.5% CHAPS surfactant): state of adhesion was scarcely observed (n=5).
(8) Group with application of anti-adhesion material (treatment with 1% Triton X-100 surfactant): state of adhesion was scarcely observed (n=5).

Example 5

Decellularized tissues were prepared by a method of a high hydrostatic pressure. A polyethylene bag was charged with porcine pericardium, bovine pericardium, porcine diaphragm, porcine peritoneum, porcine bladder or porcine dermis together with a saline and sealed. Using Dr. Chef (manufactured by Kobe Steel, Ltd.), treatment with a high hydrostatic pressure of 3,000 to 10,000 atm was performed. The porcine pericardium, the bovine pericardium, the porcine diaphragm, the porcine peritoneum, the porcine bladder or the porcine dermis treated with a high hydrostatic pressure was washed with a washing solution containing a nuclease and a washing solution containing alcohol.

An anti-adhesion material comprising decellularized tissues and fibrin glue was prepared as described below. The decellularized pericardium, the decellularized diaphragm, the decellularized peritoneum, the decellularized bladder and the decellularized dermis were incised into 3.0 cm×2.5 cm to prepare decellularized tissues. Fibrin glue was coated to both sides of the decellularized tissues to prepare anti-adhesion materials. Fibrin glue was prepared by mixing 80 mg/mL of a fibrinogen solution and 250 U/mL of a thrombin solution using a coating coatcator. A fibrinogen solution was prepared using lyophilized powder of fibrinogen contained in Bolheal and a fibrinogen solvent. A thrombin solution was prepared using lyophilized powder of thrombin contained in Bolheal and a thrombin solvent. Seprafilm (registered trade mark; manufactured by Sanofi), clinical use of which has been approved in Japan, was used as an existing anti-adhesion material.

A heart tissue adhesion model was prepared using Japanese White male rabbits of 5-6 month old. Under anesthesia with xylazine and ketamine hydrochloride, a tracheal tube was intubated into the trachea and linked to an artificial respirator. The sternum was incised 5 cm with the second to fifth rib notch being as a guide. The pericardium just under the open chest was incised by 2.0 cm×1.5 cm. The epicardium was in contact with metal file for 10 minutes. The sternum, the rib, the muscle and the skin at the open chest wound were sutured to close the chest. After the rabbits were bred normally for a month, the chest was opened and the adhesion condition between the abraded part of epicardium and the chest walls was assessed. The adhesion was scored based on a severity of dissection between the abraded part of epicardium and the chest walls in accordance with the following criteria.
Adhesion grade 0: No state of adhesion
Adhesion grade 1: State of adhesion can be dissected easily
Adhesion grade 2: State of adhesion can be dissected bluntly
Adhesion grade 3: State of adhesion needs be dissected sharply
In Example 5, the following test groups were assessed.
(1) Control group;
(2) Fibrin glue group;
(3) Decellularized tissue (porcine pericardium) group;
(4) Anti-adhesion material (porcine pericardium) group;
(5) Anti-adhesion material (bovine pericardium) group;
(6) Anti-adhesion material (porcine diaphragm) group;
(7) Anti-adhesion material (porcine peritoneum) group;
(8) Anti-adhesion material (porcine bladder) group;
(9) Anti-adhesion material (porcine dermis) group;
(10) Seprafilm group Group (1) is a group with no application of an anti-adhesion material. For application of group (2), 80 mg/mL of a fibrinogen solution and 250 U/mL of a thrombin solution were mixed at a ratio of 1:1 using a coating applicator and the mixture was coated to the epicardium of defect of the pericardium. For application of groups (3) to (9), self-pericardium adjacent to defect of the pericardium and each of the test groups were sutured to each other for fixation. For application of group (10), Seprafilm was attached to the epicardium of defect of the pericardium. The results of assessment of adhesion score are shown below.
(1) Control group: Adhesion grade 3, 3, 3, 3 (n=4)
(2) Fibrin glue group: Adhesion grade 3, 3, 2 (n=3)
(3) Decellularized tissue (porcine pericardium) group: Adhesion grade 3, 3, 1, 0 (n=4)
(4) Anti-adhesion material (porcine pericardium) group: Adhesion grade 0, 0, 0, 0 (n=4)
(5) Anti-adhesion material (bovine pericardium) group: Adhesion grade 0, 0, 0, 0, 0 (n=5)
(6) Anti-adhesion material (porcine diaphragm) group: Adhesion grade 2, 0, 0, 0, 0 (n=5)
(7) Anti-adhesion material (porcine peritoneum) group: Adhesion grade 0, 0, 0, 0, 0 (n=5)
(8) Anti-adhesion material (porcine bladder) group: Adhesion grade 0, 0, 0, 0, 0 (n=5)
(9) Anti-adhesion material (porcine dermis) group: Adhesion grade 0, 0, 0, 0, 0 (n=5)
(10) Seprafilm group: Adhesion grade 3, 3, 2 (n=3)

As is clear from the results shown above, a quite excellent anti-adhesion effect was proved by complexation of decellularized tissues and fibrin glue. The anti-adhesion materials of the present invention (porcine pericardium, bovine pericardium, porcine peritoneum, porcine bladder and porcine dermis) showed significant difference from all of control group, fibrin glue group, decellularized tissue group and Seprafilm group by Mann-Whitney's U test (*: p<0.05). The anti-adhesion material of the present invention (porcine diaphragm) showed significant difference from all of control group, fibrin glue group and Seprafilm group by Mann-Whitney's U test (*: p<0.05). These results show that a combination of decellularized tissues and fibrin glue acted as a substitute pericardium to prove the effect of the present invention as a substitute biomembrane.

Example 6

Decellularized tissue was prepared by a method of a high hydrostatic pressure. A polyethylene bag was charged with porcine pericardium together with a saline and sealed. Using Dr. Chef (manufactured by Kobe Steel, Ltd.), treatment with a high hydrostatic pressure of 3,000 to 10,000 atm was performed. The porcine pericardium treated with a high hydrostatic pressure was washed with a washing solution containing a nuclease and a washing solution containing alcohol.

An anti-adhesion material comprising decellularized tissues and fibrin glue was prepared as described below. The decellularized pericardium was incised into 2.0 cm×2.0 cm to prepare decellularized tissue. Fibrin glue was coated to both sides of the decellularized tissue to prepare anti-adhesion material. Fibrin glue was prepared by mixing 80 mg/mL of a fibrinogen solution and 250 U/mL of a thrombin solution using a coating applicator. A fibrinogen solution was prepared using lyophilized powder of fibrinogen contained in Bolheal and a fibrinogen solvent. A thrombin solution was prepared using lyophilized powder of thrombin contained in Bolheal and a thrombin solvent.

An intraperitoneal tissue adhesion model was prepared using SD male rats of 8-9 week old. Under anesthesia with medetomidine hydrochloride and ketamine hydrochloride, abdominal surgery was performed by incising the abdomen about 3 cm downward starting from about 2.5 cm under the xiphoid process along the midline. The cecum was exposed and the interior of the circle of 1.5 cm diameter on its surface was abraded 50 times with gauze and then the abraded part was further abraded 50 times with scalpel blade to cause petechial hemorrhage. Then, the interior of the circle of 1.5 cm diameter on the surface of the abdominal wall adjacent to the abraded part of the cecum was cauterized with electric scalpel. The abraded part of the cecum and the cauterized part of the abdominal wall were fixed together at four points with 7-0 Nylon suture so that both parts were in contact with each other. The abdominal wall and the skin at the open abdominal wound were sutured to close the abdomen. After the rats were bred normally for 30 days, the abdomen was opened and the adhesion condition between the abraded part of the cecum and the cauterized part of the abdominal wall was assessed. The adhesion was scored based on a severity of dissection between the abraded part of the cecum and the cauterized part of the abdominal wall, an amount of bleeding, an area of adhesion and the type of adhesion in accordance with the criteria shown in Table 1. Adhesion score was a total of the respective scores of assessment items A to D.

TABLE 2

| Right: Score Below: assessment items | 0 | 1 | 2 | 3 | 4 |
|---|---|---|---|---|---|
| A: Extent of dissection | None | Easy | Blunt dissection is necessary | Sharp dissection is necessary | — |
| B: Amount of bleeding during dissection | None | Trace amount | Small amount (less than 0.5 g) | Large amount (0.5 g or more) | — |
| C: Area of adhesion | 0% | 25% or less | 50% or less | 75% or less | Over 75% |
| D: Type | None | Transparent No blood vessel | Semi-transparent Capillary blood vessel | Opaque Small blood vessel | Opaque Large blood vessel |

In Example 6, the following treatment groups were assessed.
(1) Control group;
(2) Anti-adhesion material Anti-adhesion material (2) was fixed between the abraded part of the cecum and the cauterized part of the abdominal wall. The results of assessment of adhesion score are shown in Table 3 wherein adhesion score is shown as a total of the respective scores of A to D of Table 1.

TABLE 3

| Test group | No. of animals | Adhesion score | | | | Total of A to D | Mean value ± SD |
|---|---|---|---|---|---|---|---|
| | | A | B | C | D | | |
| Control | 5 | 3 | 2 | 4 | 3 | 12 | 11.2 ± 0.8 |
| | | 2 | 2 | 4 | 3 | 11 | |
| | | 2 | 2 | 4 | 3 | 11 | |
| | | 2 | 1 | 4 | 3 | 10 | |
| | | 3 | 2 | 4 | 3 | 12 | |
| Anti-adhesion material | 5 | 1 | 1 | 2 | 2 | 6 | 6.6 ± 1.3 |
| | | 1 | 1 | 2 | 2 | 6 | |
| | | 1 | 1 | 1 | 2 | 5 | |
| | | 1 | 1 | 4 | 2 | 8 | |
| | | 1 | 1 | 4 | 2 | 8 | |

As is clear from Table 3, a quite excellent anti-adhesion effect was proved also in the abdomen by complexation of decellularized tissues and fibrin glue. The anti-adhesion materials of the present invention showed significant difference from control group by Mann-Whitney's U test (*: $p<0.01$).

Example 7

1. Preparation of Decellularized Tissues

Decellularized tissues were prepared by a method of a high hydrostatic pressure. A polyethylene bag was charged with bovine pericardium together with a saline and sealed. Using Dr. Chef (manufactured by Kobe Steel, Ltd.), treatment with a high hydrostatic pressure of 3,000 to 10,000 atm was performed. The bovine pericardium treated with a high hydrostatic pressure was washed with a washing solution containing a nuclease and a washing solution containing alcohol to give decellularized tissues derived from bovine pericardium. A film thickness of the decellularized tissues was 400 μm.

2. Preparation of Anti-Adhesion Materials (Complexation of Decellularized Tissues and Fibrin Glue)

The decellularized tissues obtained in 1 above were lyophilized and then fibrin glue was coated to both sides of the decellularized tissues to prepare anti-adhesion materials. Fibrin glue was prepared by mixing 80 mg/mL of a fibrinogen solution and 250 U/mL of a thrombin solution using a coating applicator. A fibrinogen solution was prepared using lyophilized powder of fibrinogen contained in Bolheal and a fibrinogen solvent. A thrombin solution was prepared using lyophilized powder of thrombin contained in Bolheal and a thrombin solvent.

3. Experiment with Rabbit Peritoneum Adhesion Model

Experiment with peritoneum adhesion model was performed using Japanese White male rabbits of 15-20 month old as described below. First, after anesthetic treatment, body hair at the abdomen was removed and the skin surface of the abdomen was disinfected. The disinfected skin was incised with scalpel to separate the skin from the abdominal wall. The abdominal wall was removed by 1.5 cm×2 cm to check the position of the cecum. The surface of the cecum was cauterized with electric scalpel. With the cauterized part of the cecum being positioned to the body surface, the cecum was fixed to the defective part of the abdominal wall by suture. An anti-adhesion material of 2 cm×2.5 cm was sutured to the defective part of the abdominal wall. Closing the wound of the tunica muscularis and the skin, awakening measures were done. After confirming walking, the rabbits were brought back a breeding cage and were bred for a fixed period of time.

After a week of a test period of normal breeding, the abdomen was opened and the adhesion condition between the anti-adhesion material and the cecum was assessed. The adhesion was scored based on a severity of dissection between the anti-adhesion material and the cecum in accordance with the following criteria. The results of assessment are shown in Table 4.

<Criteria for Assessing Anti-Adhesion Effect>
Adhesion grade 0: No state of adhesion
Adhesion grade 1: State of adhesion can be dissected easily
Adhesion grade 2: State of adhesion can be dissected bluntly
Adhesion grade 3: State of adhesion requires sharp dissection Example 8

The procedures were carried out as in Example 7 excepting that a test period of normal breeding was changed from a week to four weeks. The results of assessment are shown in Table 4.

Example 9

The procedures were carried out as in Example 7 excepting that the decellularized tissues were changed from the decellularized tissue of bovine pericardium to the decellularized tissue of porcine small intestine submucosal tissue and that a film thickness of the decellularized tissue was 100 µm. The results of assessment are shown in Table 4.

Example 10

The procedures were carried out as in Example 9 excepting that a test period of normal breeding was changed from a week to four weeks. The results of assessment are shown in Table 4.

Comparative Example 5

The decellularized tissues obtained in Example 7, Preparation of decellularized tissues, were used without complexation with fibrin glue to conduct experiment with rabbit peritoneum adhesion model. A test period of normal breeding was a week. The results are shown in Table 4.

Comparative Example 6

The decellularized tissues obtained in Example 7, Preparation of decellularized tissues were used without complexation with fibrin glue to conduct experiment with rabbit peritoneum adhesion model. A test period of normal breeding was four weeks. The results are shown in Table 4.

TABLE 4

| | Decellularized tissues from: | Film thickness | Complexation | Test period | * |
|---|---|---|---|---|---|
| Ex. 7 | Bovine pericardium | 400 µm | Coating of fibrin glue | 1 week | 1 |
| Ex. 8 | Bovine pericardium | 400 µm | Coating of fibrin glue | 4 weeks | 1 |
| Ex. 9 | Porcine small intestine submucosal tissue | 100 µm | Coating of fibrin glue | 1 week | 0 |
| Ex. 10 | Porcine small intestine submucosal tissue | 100 µm | Coating of fibrin glue | 4 weeks | 2 |
| Comp. Ex. 5 | Bovine pericardium | 400 µm | — | 1 week | 3 |
| Comp. Ex. 6 | Bovine pericardium | 400 µm | — | 4 weeks | 3 |

* Assessment of anti-adhesion effect

From the results shown in Table 4, it is found that the anti-adhesion material of the present invention has an excellent anti-adhesion effect.

INDUSTRIAL APPLICABILITY

The present invention can be used as an anti-adhesion material, in particular, a substitute biomembrane accompanied by tissue regeneration.

The invention claimed is:

1. An anti-adhesion material comprising decellularized tissues and a biocompatible polymer selected from the group consisting of alginic acid, gelatin, fibrin glue and polyethylene glycol,
    wherein the decellularized tissues are those prepared by decellularizing biological tissues selected from the group consisting of pericardium, bladder, amnion, dura mater, peritoneum, diaphragm, fascia, small intestine submucosa and skin,
    wherein the biocompatible polymer and the decellularized tissue are complexed to each other, and
    wherein the anti-adhesion material reduces adhesion to biological tissues.

2. The anti-adhesion material of claim 1 wherein the decellularized tissues are the ones prepared by treating biological tissues with a high hydrostatic pressure or with a surfactant.

3. The anti-adhesion material of claim 2 wherein the treatment with a high hydrostatic pressure comprises applying a hydrostatic pressure of 50 to 1,500 MPa to biological tissues in a medium.

4. The anti-adhesion material of any one of claim 1, claim 2 or claim 3 wherein the biocompatible polymer is a biocompatible polymer which naturally occurs.

5. The anti-adhesion material of any one of claim 1, claim 2 or claim 3 wherein the biocompatible polymer is fibrin glue.

6. The anti-adhesion material of claim 1 wherein the complexation of the biocompatible polymer to the decellularized tissues is immersion or coating of the biocompatible polymer to the decellularized tissues.

7. The anti-adhesion material of any one of claim 1, claim 2, or claim 3 wherein the anti-adhesion material is an anti-adhesion membrane and a film thickness is 10 to 5,000 µm.

8. An anti-adhesion material kit comprising decellularized tissues and a biocompatible polymer selected from the group consisting of alginic acid, gelatin, fibrin glue and polyethylene glycol, wherein the decellularized tissues are those prepared by decellularizing biological tissues selected from the group consisting of pericardium, bladder, amnion, dura mater, peritoneum, diaphragm, fascia, small intestine submucosa and skin, wherein the biocompatible polymer and the decellularized tissue are complexed to each other, and wherein the anti-adhesion material reduces adhesion to biological tissues.

9. The kit of claim 8 wherein the decellularized tissues are the ones prepared by treating biological tissues with a high hydrostatic pressure or with a surfactant.

10. The kit of claim 9 wherein the treatment with a high hydrostatic pressure comprises applying a hydrostatic pressure of 50 to 1,500 MPa to biological tissues in a medium.

11. The kit of any one of claim 8, claim 9 or claim 10 wherein the biocompatible polymer is fibrin glue.

12. The kit of claim 8 wherein the complexation of the biocompatible polymer to the decellularized tissues is immersion or coating of the biocompatible polymer to the decellularized tissues.

13. The kit of any one of claim 8, claim 9, or claim 10 wherein the anti-adhesion material is an anti-adhesion membrane and a film thickness is 10 to 5,000 μm.

14. A substitute biomembrane comprising decellularized tissues and a biocompatible polymer selected from the group consisting of alginic acid, gelatin, fibrin glue and polyethylene glycol, wherein the decellularized tissues are those prepared by decellularizing biological tissues selected from the group consisting of pericardium, bladder, amnion, dura mater, peritoneum, diaphragm, fascia, small intestine submucosa and skin, wherein the biocompatible polymer and the decellularized tissue are complexed to each other, and wherein the substitute biomembrane reduces adhesion to biological tissues.

15. The substitute biomembrane of claim 14 wherein the decellularized tissues are the ones prepared by treating biological tissues with a high hydrostatic pressure or with a surfactant.

16. The substitute biomembrane of claim 15 wherein the treatment with a high hydrostatic pressure comprises applying a hydrostatic pressure of 50 to 1,500 MPa to biological tissues in a medium.

17. The substitute biomembrane of any one of claim 14, claim 15 or claim 16 wherein the biocompatible polymer is a biocompatible polymer which naturally occurs.

18. The substitute biomembrane of any one of claim 14, claim 15 or claim 16 wherein the biocompatible polymer is fibrin glue.

19. The substitute biomembrane of claim 14 wherein the complexation of the biocompatible polymer to the decellularized tissues is immersion or coating of the biocompatible polymer to the decellularized tissues.

20. The substitute biomembrane of any one of claim 14, claim 15 or claim 16 wherein a film thickness is 10 to 5,000 μm.

21. A method for preparing a substitute biomembrane comprising complexing a biocompatible polymer selected from the group consisting of alginic acid, gelatin, fibrin glue and polyethylene glycol, to decellularized tissues, wherein the decellularized tissues are those prepared by decellularizing biological tissues selected from the group consisting of pericardium, bladder, amnion, dura mater, peritoneum, diaphragm, fascia, small intestine submucosa and skin, wherein the biocompatible polymer and the decellularized tissue are complexed to each other, and wherein the substitute biomembrane reduces adhesion to biological tissues.

22. The method of claim 21 wherein the complexation is immersion or coating of the biocompatible polymer to the decellularized tissues.

23. A substitute biomembrane kit comprising decellularized tissues and a biocompatible polymer selected from the group consisting of alginic acid, gelatin, fibrin glue and polyethylene glycol, wherein the decellularized tissues are those prepared by decellularizing biological tissues selected from the group consisting of pericardium, bladder, amnion, dura mater, peritoneum, diaphragm, fascia, small intestine submucosa and skin, wherein the biocompatible polymer and the decellularized tissue are complexed to each other, and wherein the substitute biomembrane reduces adhesion to biological tissues.

24. The kit of claim 23 wherein the decellularized tissues are the ones prepared by treating biological tissues with a high hydrostatic pressure or with a surfactant.

25. The kit of claim 24 wherein the treatment with a high hydrostatic pressure comprises applying a hydrostatic pressure of 50 to 1,500 MPa to biological tissues in a medium.

26. The kit of any one of claim 23 wherein the biocompatible polymer is fibrin glue.

27. The kit of claim 23 wherein the complexation of the biocompatible polymer to the decellularized tissues is immersion or coating of the biocompatible polymer to the decellularized tissues.

28. The kit of any one of claim 23 wherein a film thickness of the substitute biomembrane is 10 to 5,000 μm.

* * * * *

UNITED STATES PATENT AND TRADEMARK OFFICE
CERTIFICATE OF CORRECTION

Page 1 of 1

PATENT NO. : 11,033,661 B2
APPLICATION NO. : 15/556776
DATED : June 15, 2021
INVENTOR(S) : Hideki Saga et al.

It is certified that error appears in the above-identified patent and that said Letters Patent is hereby corrected as shown below:

On the Title Page

Please add the following Assignee to (73) Assignees:
--KM BIOLOGICS CO., LTD., Kumamoto (JP)--

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*